United States Patent
Seemayer et al.

(10) Patent No.: US 6,861,526 B2
(45) Date of Patent: Mar. 1, 2005

(54) PROCESS FOR THE PREPARATION OF (S, S)-CIS-2-BENZHYDRYL-3-BENZYLAMINOQUINUCLIDINE

(75) Inventors: Robert Seemayer, Palo Alto, CA (US); Thomas C. Nugent, San Francisco, CA (US)

(73) Assignees: Pfizer Inc., New York, NY (US); DSM Pharmaceuticals, Inc., Greenville, NC (US)

( * ) Notice: Subject to any disclaimer, the term of this patent is extended or adjusted under 35 U.S.C. 154(b) by 0 days.

(21) Appl. No.: 10/679,961

(22) Filed: Oct. 6, 2003

(65) Prior Publication Data

US 2004/0116704 A1 Jun. 17, 2004

Related U.S. Application Data

(60) Provisional application No. 60/419,051, filed on Oct. 16, 2002.

(51) Int. Cl.[7] ............................................. C07D 453/02
(52) U.S. Cl. ....................................................... 546/133
(58) Field of Search ........................................ 546/133

(56) References Cited

U.S. PATENT DOCUMENTS

| | | | |
|---|---|---|---|
| 4,680,283 A | 7/1987 | Veber et al. ................... | 514/17 |
| 5,138,060 A | 8/1992 | Godek et al. ................ | 546/133 |
| 5,162,339 A | 11/1992 | Lowe, III .................... | 514/305 |
| 5,721,255 A | 2/1998 | Howard et al. ............. | 514/329 |
| 5,939,433 A | 8/1999 | Ito et al. ..................... | 514/305 |
| 5,939,434 A | 8/1999 | Satake ......................... | 514/305 |

FOREIGN PATENT DOCUMENTS

| | | |
|---|---|---|
| WO | 9220676 | 11/1992 |
| WO | 9221677 | 12/1992 |
| WO | 9408997 | 4/1994 |
| WO | 9410170 | 5/1994 |
| WO | 9411368 | 5/1994 |
| WO | 9426740 | 11/1994 |
| WO | 9703984 | 2/1997 |

OTHER PUBLICATIONS

Clemo, G. R. and E. Hoggarth. "Synthesis of 5–Substituted Rubans." *Journal of Chemical Society* (London), 1939, pp. 1241–1244.

Lowe, III, J. A. et al. "The Discovery of (2S, 3S)–cis–2–(Diphenylmethyl)–N–[(2–methoxyphenyl)methyl]–1–azabicyclo[2.2.2]octan–3–amine as a Novel, Nonpeptide Substance P Antagonist." *J. Med. Chem.*, 1992, 35, pp. 2591–2600.

Warawa, E. J. et al. "Quinuclidine Chemistry.4.[1] Diuretic Properties of cis–3–Amino–2–benzhydrylquinuclidine." *J. Med. Chem.*, 1975, 18 (6), pp. 587–593.

Seward, E. M., "Quinuclidine–Based NK–1 Antagonists 1: 3–Benzyloxy–1–Arabicyclo[2.2.2]Octanes", *Bioorganic & Medical Chemistry Letters*, vol. 3, No. 6, pp. 1361–1366, 1993.

*Primary Examiner*—Patricia L. Morris
(74) *Attorney, Agent, or Firm*—Ladas & Parry LLP

(57) ABSTRACT

A process for preparing (S,S)-cis-2-benzhydryl-3-benzylaminoquinuclidine. The process includes the steps of contacting a compound containing a mixture of R- and S-isomers and having the formula

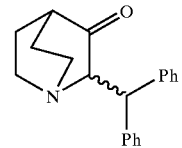

with an effective amount of a chiral organic acid in the presence of an organic solvent and an effective amount of an organic carboxylic acid for converting the R-isomer into an acid salt of the S isomer, wherein the organic solvent is capable of solubilizing the compound containing the mixture of R- and S-isomers, while precipitating the acid salt and the organic carboxylic acid is different from the chiral organic acid; neutralizing the acid salt with a base to provide an S-isomer of a chiral ketone of the formula

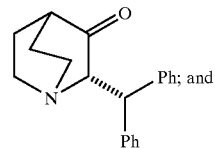

; and reacting the chiral ketone with an organic amine in the presence of a Lewis acid to provide the corresponding imine and reducing the imine.

30 Claims, No Drawings

PROCESS FOR THE PREPARATION OF (S, S)-CIS-2-BENZHYDRYL-3-BENZYLAMINOQUINUCLIDINE

This application claims the benefit of U.S. Provisional Application No.: 60/419,051 filed Oct. 16, 2002 and incorporates the same by reference.

FIELD OF THE INVENTION

The present invention relates to the method of the preparation of the title compound, (S,S)-cis-2-benzhydryl-3-benzylaminoquinuclidine (4) which is a useful intermediate in the preparation of optically active quinuclidine analogues which have utility as non-peptide antagonists of Substance P.

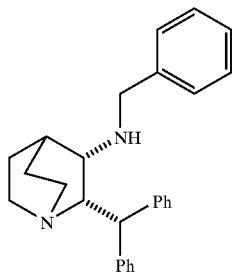

4

BACKGROUND OF THE INVENTION

Substance P is a naturally occurring undecapeptide belonging to the tachykinin family of peptides, members of which exert prompt stimulatory action on smooth muscle tissue. Substance P is a pharmaceutical active neuropeptide that is produced in mammals and possesses a characteristic amino acid sequence that is illustrated in U.S. Pat. No. 4,680,283. A variety of substance P antagonists could be prepared from the title compound; for example, U.S. Pat. No. 5,162,339 describes Substance P antagonists of formula 2 where $R^1$ is methoxy and $R^2$ is independently selected from the group consisting of isopropyl, tert-butyl, methyl, ethyl, and sec-butyl.

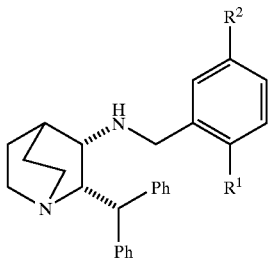

2

These substance P antagonists can be prepared by the reductive amination of cis-2-benzhydryl-3-amino-quinuclidine 1

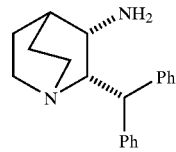

1 using the appropriate aldehyde of the formula $R^3$CHO where $R^3$ is defined as a benzaldehyde derivative with the phenyl ring substituted with $R^1$ and $R^2$ as described above, This reductive amination may be achieved with a variety of reagents such as hydrogen in the presence of a suitable metal catalyst, sodium cyanoborohydride, sodium triacetoxyborohydride, sodium borohydride, zinc and hydrochloric acid, borane dimethylsulfide or formic acid as described, for example, in WO92/21677, WO94/10170, WO94/11368, WO94/26740, WO94/08997WO97/03984, and U.S. Pat. Nos. 5,162,339, 5,721,255, 5,939,433, and 5,939,434. An alternative strategy is the conversion of 1 to 2 by an alkylation with an appropriate electrophile as is taught, for example, in U.S. Pat. Nos. 5,807,867 and 5,939,433 and WO92/21677. A further alternative strategy for the conversions of 1 to 2 is the acylation of 1 with an activated carboxylic acid derivative followed by reduction of the resultant amide with a reagent such as lithium aluminum hydride as described in WO92/21677 and the Journal of Medicinal Chemistry, 35, 2591 (1992).

The cis-2-benzhydryl-3-amino-quinuclidine 1, which is an intermediate in the formation of 2, is available from the 3-benzylamine-2-benzhydryl-quinuclidine 4 by debenzylation with hydrogen gas and a catalyst. A process for preparing benzylamine 4 has been described by Warawa in the Journal of Medicinal Chemistry, 18, 587 (1975) and is illustrated in Scheme 1. The process starts with 3-quinuclidinone 5, available by the method of Clemo et al in the *Journal of the Chemical Society* (London) p1241 (1939), which is condensed with benzaldehyde to generate enone 6. In turn, this is reacted with phenylmagnesium chloride to form 2-benzhydryl-3-quinuclidinbne 3. Reductive alkylation of ketone 3 with benzylamine provides 4.

SCHEME 1

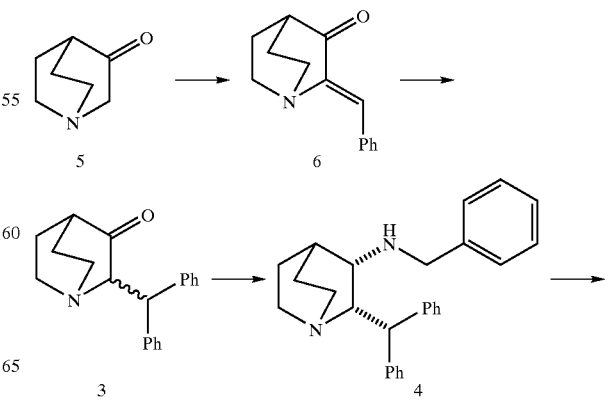

-continued

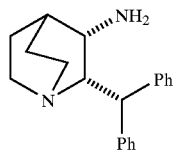

1

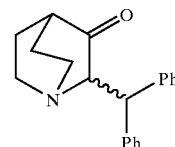

5

The approach is amenable to adaptation to allow access to aryl and quinuclidine analogs as described in WO92/20676 and U.S. Pat. No. 5,162,339. The use of methoxybenzylamine has been used in place of benzylamine as this allows for hydrolytic removal to afford the amine 1 as well as hydrogenolysis, as described in U.S. Pat. Nos. 5,807,867 and 5,939,433.

The use of 9-BBN to effect the imine reduction formed from the reaction of benzylamine with the ketone 3 has been advocated as this maximizes formation of the desired cis-isomer of 4. This procedure is described in the Journal of Medicinal Chemistry, 35, 2591 (1992).

In all of these examples, the materials were racemic. The separation of enantiomers has been done on compound 1, 2, or 4 by classical resolution techniques. This is illustrated by the methodology described, for example, in U.S. Pat. No. 5,138,060, where the methoxyphenyl derivative 7 is separated to provide the desired (−)-isomer by crystallization of racemic 7 with (−)-mandelic acid from ethyl acetate, purification of the salt by subsequent recrystallization from ethyl acetate, and release of, the free amine product by treatment with base. In a related procedure, N-[[2-methoxy-5-(1-methylethyl)phenyl]methyl]-2-(diphenylmethyl)-1-azabicyclo[2.2.2]octan-3-amine is resolved by use of (1R)-(−)-10-camphorsulfonic acid, as described in WO 97/03984.

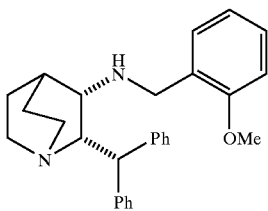

7

Use of D-tartaric acid has been disclosed in Japanese Patent No. 07025874 by Murakami, et al. for the resolution of cis-3-amino-2-benzhydrylquinuclidine (1) in methanol. Separation of the diastereoisomers of an intermediate carbamate have also been used to obtain 1 as a single enantiomer as described in the Journal of Medicinal Chemistry, 35, 2591 (1992).

SUMMARY OF THE INVENTION

The present invention relates to a process for the preparation of (S,S)-cis-2-benzhydryl-3-benzylamino quinuclidine. The inventive process includes contacting a compound containing a mixture of R- and S-isomers and having the formula with an effective amount of a chiral organic acid in the presence of an organic solvent and an effective amount of an organic carboxylic acid for converting the R-isomer into an acid salt of the S isomer. In accordance with the inventive method, the organic solvent employed is capable of solubilizing the compound containing the mixture of R- and S-isomers, while precipitating the acid salt. Moreover, the organic carboxylic acid employed in the inventive process is different from the chiral organic acid employed.

The contacting step mentioned above is performed such that a dynamic kinetic resolution is occurring. That is, the inventive contacting step is carried out using reactants and conditions which drive the reaction to the formation of the S isomer. In accordance with the present invention, this dynamic kinetic resolution is obtainable when an effective amount of the organic carboxylic acid is employed to solubilize the quinuclidinone and provide an acidic environment to racemize the R isomer to the S isomer. It is preferred that the organic carboxylic acid is not chiral. Preferably, at least one equivalent, of organic carboxylic acid is used, and more preferably greater than one equivalent is used relative to the quinuclidinone. Likewise, the dynamic kinetic resolution is obtainable when an effective amount of at least one equivalent, preferably greater than 1 equivalent, of the chiral organic acid is employed.

After the contacting step, the resultant acid salt is neutralized with an organic base to provide an S-isomer of a chiral ketone of the formula

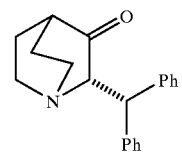

Next, the chiral ketone is reacted with an organic amine in the presence of a Lewis acid to provide the corresponding imine and then the imine is reduced. In accordance with the present invention, an effective amount of the Lewis acid, preferably at least one equivalent and, more preferably, greater than one equivalent is employed for optimal converision. The inventive reaction scheme is depicted in Scheme 2 below.

In a preferred embodiment, the starting material is racemic 2-benzhydryl-3-quinuclidinone(3). In a preferred embodiment, the process starts with racemic 2-benzhydryl-3-quinuclidinone (3) prepared as described by the method of Warawa in the Journal of Medicinal Chemistry, 18, 587 (1975). When treated with L-tartaric acid; a preferred chiral organic acid, the (S)-isomer of 3 crystallized as its tartrate salt in 85–90% yield. As a resolution can only deliver a 50% yield of one isomer, the remainder being the undesired antipode, a dynamic kinetic resolution is occurring. Thus, the undesired (R)-isomer is being converted to the (S)-isomer under the reaction conditions. The solvent for the crystallization is an alcohol in which the ketone 3 is soluble, of which ethanol is preferred, in the presence of an organic carboxylic acid, of which acetic acid is preferred.

The dynamic kinetic resolution allows for losses to be minimized compared to the classical resolution approaches taught in the literature as the undesired antipode does not have to be discarded.

The optically active ketone can be recovered from this salt and utilized in a reductive alkylation with benzylamine in a process wherein the S-stereochemistry is maintained at C-2 and the S-cis-stereochemistry is largely controlled at the new carbon nitrogen bond at C-3.

The process for the asymmetric reductive alkylation with benzylamine involves 1) formation of the intermediate imine by treatment of S-3 with benzylamine in an organic solvent in the presence of an excess of a mild Lewis acid such as aluminum tri-isopropoxide or titanium tetra-isopropoxide followed by reduction of the imine in-situ with hydrogen gas over a noble metal catalyst. Without limitation, an appropriate solvent for the reaction is tetrahydrofuran and the preferred catalyst for the hydrogenation is Pt on carbon.

SCHEME 2

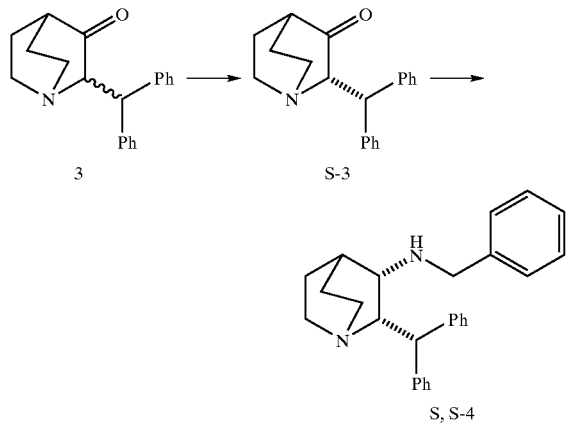

DETAILED DESCRIPTION

For those skilled in the art, the use of the reagents and methods used in the racemic series to prepare the amine 1, and analogs thereof, is an obvious extension. The invention comprises a dynamic resolution of the ketone 3 by formation of a salt with a chiral organic acid. As used herein a chiral organic acid is an organic carboxylic acid which has an asymmetric center and has stereoisomers, some of which are mirror images of each other (enantiomers). The chiral organic acid is also soluble in the organic solvent.

An effective amount of chiral organic acid is utilized. Preferably, at least about an equimolar amount of chiral organic acid to quinuclidinone is utilized, although an excess amount of chiral organic acid can be used; however, it is preferred that about an equimolar amount of chiral organic acid is utilized. Tartaric acid is the preferred example. An organic solvent in which the racemic ketone is soluble but in which the resultant salt precipitates is employed. Sufficient solvent is present to solubilize the quinuclidinone and the various reagents. This organic solvent is preferably an alcohol, where ethanol is the preferred alcohol, and denatured alcohol is the preferred form of ethanol.

A weak organic carboxylic acid is added to aid the salt formation. The organic carboxylic acid may be a mono carboxylic acid or a poly carboxylic acid, however, it is preferred that it is a mono carboxylic acid or dicarboxylic acid. It is especially preferred that it is a mono carboxylic acid. The carboxylic acid includes, but is not limited to: acetic acid, propionic acid, and butyric acid. The preferred acid is acetic acid.

As described hereinabove, the organic carboxylic acid utilized is present in amounts sufficient to effect salt formation and promote precipitation of the salt. Preferably, at least one equivalent of organic carboxylic acid is utilized relative to the quinuclidinone.

As used herein, the term "equivalent" as it relates to an acid, refers to that amount, especially in weight or moles that contains one atomic weight or mole, respectively, of acidic hydrogen, i.e., hydrogen that reacts with base during neutralization. For example, if the acid is a monocarboxylic acid, such as acetic acid, one mole acetic acid produces one mole (equivalent) of acid. However, if the carboxylic acid is a dicarboxylic acid, said as oxalic acid, succinic acid, and the like, one mole of the dicarboxylic acid produces 2 equivalents of acid.

Thus, if the organic acid is a monocarboxylic acid, it is preferred that at least about an equimolar amount of monocarboxylic acid relative to the quinuclidinone is utilized, while if the carboxylic acid is a dicarboxylic acid, it is preferred that on a molar basis, at least about twice as much quinuclidinone relative to dicarboxylic acid is utilized. However, it is preferred that excess amounts of organic carboxylic acid is utilized.

It is preferred that the quinuclidinone, the chiral organic acid and the organic carboxylic acid are mixed together at about ambient temperatures, although they may be mixed at temperatures as low as 0° C. up to the reflux temperature of the solvent. The reaction is allowed to proceed until precipitation of the (S)-salt isomer ceases, i.e., no more precipitation is observed.

Without wishing to be bound it is believed that the combination of the chiral organic acid with the quinuclidinone and the organic carboxylic acid promotes the dynamic kinetic resolution. More specifically, under the reaction conditions, not only is the salt of the S-isomer precipitating but the undesired R isomer is being converted to the S-isomer salt. Thus, since it is being converted to the S isomer, little, if any, of R isomer is discarded under the reaction conditions of the present invention.

In the second step of the invention, the chiral ketone S-3 is obtained from the tartrate salt by neutralization of the S isomer, e.g., S-tartaric acid salt. It is preferred that this second step is conducted in a biphasic mixture of an organic solvent and water. Suitable organic solvents include, but are not limited to: toluene, ethyl acetate, and methyl t-butyl ether. The preferred organic solvent is toluene. Appropriate bases for the neutralization reaction include, but are not limited to: sodium bicarbonate, potassium bicarbonate, sodium carbonate, potassium carbonate, sodium hydroxide and potassium hydroxide. In a preferred embodiment, the salt is suspended in the biphasic solvent mixture and an aqueous solution of the base is added with cooling to maintain a temperature below 25° C. until reaching a pH of about 9. The free base of optically active S-3 is recovered from the organic layer as a solid.

Without limitation one application is described herein to illustrate that the chiral ketone S-3 can be used to prepare substance P antagonists and that racemization does not occur. For those skilled in the art, other aldehydes, reducing agents for the imine and deprotection methods can be envisioned from the literature on the racemic compounds. Step three of this scheme involves the formation of the imine with a nitrogenous organic amine, such as alkyl amine, aryl amine or arylalkyl amine. It is preferred that alkyl contains 1–6 carbon atoms, which may be branched or straight chained. Examples include methyl, ethyl, isopropyl, propyl, butyl, sec-butyl, t-butyl, isobutyl, pentyl and hexyl. The term "aryl" when used alone or in combination, is an aromatic compound containing 6, 10, 14 or 18 ring carbon atoms and up to a total of 25 carbon atoms. Examples include phenyl, napthyl, and the like. The preferred amine is benzylamine. The organic amine is reacted in the presence of a mild Lewis acid in-situ to form the imine, which is then reduced to the corresponding amine by techniques known to one of ordinary skill in the art, such by reduction over a noble metal catalyst and hydrogen. This approach avoids possible racemization during the conversion of S-3 to S-4. Imine formation in the presence of a Br+e,sez o+ee nsted acid resulted in some racemization at C-2. Epimerization is not observed if a Lewis acid is used to catalyze formation of the imine and then the reduction is directly performed on the resultant mixture.

Solvents suitable for the imine formation reaction are any homogenate hydrocarbons such as methylene chloride, dichlorobenzene, chlorobenzene, dichloroethane, or other inert solvents such as ethereal solvents including, but not limited to: THF and hydrocarbons including, but not limited to: toluene. Appropriate Lewis acids include aluminum tri-isopropoxide and titanium tetra-isopropoxide. The preferred Lewis acid is aluminum tri-isopropoxide. The Lewis acid is present in amounts effective to form the imine. It is preferred that the nitrogenous organic amine is present in at least about equimolar amounts to that of Ketone S-3, but an excess of amine may be present. Moreover, it is preferred that the Lewis acid is present in at least catalytic effective amounts to help convert the ketone S-3 to the imine. Preferably, Lewis acid is present in at least equimolar amounts to that of the ketone S-3, especially if the latter is the limiting reagent. The resulting imine is reduced by standard techniques, such as by using a noble metal catalyst and hydrogen. The noble metal catalysts include platinum and palladium metals on various supports. The preferred catalyst is platinum on carbon. For example, one embodied step of the inventive process is carried out by mixing S-3 and benzylamine in tetrahydrofuran as a solvent and aluminum tri-isopropoxide as the Lewis acid. The imine formation is preferably carried out at room temperature for three hours. A slurry of 5% Pt/C in tetrahydrofuran was added and the reaction is stirred under a hydrogen atmosphere at 75 psi of hydrogen pressure for 15 hours. Optically active S,S-4 was isolated from the reaction.

The above-described process of the present invention achieves a significant advantage over the conventional, classical resolution approaches. The yield of the resolution step, i.e., the first contacting step, is greater than 50%, which is the maximum that can be achieved with by a typical resolution. The undesired isomer is converted to the desired one, which is isolated from the mixture, under the reaction conditions. This results in increased throughput and cost savings. The use of the quinuclidinone as a single enantiomer allows for asymmetric synthesis of the Substance P antagonists in an optically pure form by a variety of routes and alleviates the problems associated with late stage resolutions. The problems associated with racemization during reductive amination are eliminated by the use of a Lewis acid to catalyze imine formation and in situ catalytic hydrogenation.

The process described herein is useful for preparing the S,S-cis-2-benzhydryl-3-benzyl-aminoquinuclidinone from a mixture of R and S isomers of quinuclidinone. The R isomer may be present in greater amounts or vice versa. The above process is also applicable to the formation of the title compound from racemic 2-benzhydryl-3-quinuclidinone, which typically is the usual starting material.

The product formed by the above-identified process is substantially enantiomerically pure, that is, substantially free from any other stereoisomers, i.e., the RR, RS or SR products. Preferably, it contains less than 10% impurity from the other stereoisomers, and more preferably, less than about 5% impurity from the other stereoisomers and even more preferably, less than about 1% of the other stereoisomers.

The product thus formed is also preferably substantially pure, i.e., contains less than 10% impurity and more preferably contains less than 5% impurity. However, if desired, the (S,S)-cis-2-benzhydryl-3-benzylaminoquinuclidine thus formed can be further purified by techniques known in the art, e.g., chromatography, including HPLC preparative chromatography, and other column chromotagraphy, recrystallization and the like.

The examples that follow are intended as an illustration of certain preferred embodiments of the invention, and no limitation of the invention is implied.

EXAMPLE 1

(2S)-Benzhydryl-3-quinuclidinone L-tartaric acid salt

Racemic 2-benzhydryl-3-quinuclidinone (52.45 g, 180 mmol) was dissolved in denatured ethanol (525 ml) with acetic acid (10.4 ml, 180 mmol) and L-tartaric acid (27 g, 180 mmol) was added. The mixture was heated to reflux for 12 hours and then allowed to cool to room temperature and held for one hour. The solids were collected and dried under vacuum at 40° C. for 12 hours. The yield of the desired salt was 69.9 g, 88% of theory.

EXAMPLE 2

(2S)-Benzhydryl-3-quinuclidinone (S-3)

The L-tartaric acid salt from the previous example (69.9 g, 158 mmol) was suspended in toluene (700 ml) and cooled with an ice water bath while a saturated solution of sodium bicarbonate (500 ml) was added dropwise while maintaining a maximum temperature of 25° C. The clear, biphasic mixture was stirred for 20 minutes at 25° C. and the layers were separated. The organic layer was washed with water (100 ml), the layers were separated and the organics dried over sodium sulfate. The organics were filtered and evaporated in vacuo to provide the desired, optically active ketone as a colorless solid, 45.66 g; 99% yield. Mp 145–146° C. $^1$HMR (300 MHz, CDCl$_3$) δ 1.86–2.00 (m, 4), 2.41–2.43 (m, 1), 2.54–2.59 (m, 2), 3.08 (t, 2), 3.98 (d, 1), 4.55 (d, 1), 7.17 (m, 8), 7.38–7.41 (m, 2).

EXAMPLE 3

(S,S)-2-Benzylhydryl-3-benzylamino-quinuclidine (S,S-4)

With aluminum tri-isoproxide:

Under nitrogen, (2S)-benzhydryl-3-quinuclidinone (0.50 g, 1.0 equiv, 1.72 mmol) was dissolved in anhydrous THF (2 mL). Benzylamine (0.21 mL, 1.1 equiv, 1.89 mmol) was then added followed by a solution of aluminum isopropoxide (0.42 g, 1.2 equiv, 2.06 mmol) in 2 mL of anhydrous THF. The solution was stirred for 3 hours. To this colorless solution was then added a slurry of 5% Pt/C (0.063 g, Degussa F101RA/W, ~60% wet) in 1 mL anhydrous THF. The reaction was placed in a Parr reactor, pressurized to 75 psi H$_2$ and allowed to react at room temperature for 15 hours. The reaction mixture was poured into 15 mL of 2M HCl, followed by filtration, basification with 1M NaOH and extraction with 50 mL methyl tertiary butyl ether (MTBE). The MTBE layer was dried with MgSO$_4$, followed by removal of solvent in vacuo leaving a white crystalline solid. This was analyzed as all cis isomer (<2% trans isomer), >99% ee (none of other enantiomer observed)

With titanium tetra-isoproxide:

(2S)-Benzhydryl-3-quinuclidinone (9.00 g, 30.9 mmol) was dissolved in 75 mL of anhydrous THF. The solution is transferred through a port to a 300 mL autoclave with the hydrogenation head secured while maintaining a positive flow of nitrogen. Through the same port on the hydrogenator head and under 300 rpm stirring benzylamine (3.7 mL, 33.9 mmol) was added followed by titanium (IV) isopropoxide (10.9 mL, 36.9 mmol). The port is closed and the autoclave is pressure tested (150 psi nitrogen) while the reaction mixture is stirred at 300 rpm. After 3.0 hours at 25° C. the pressure is released and under positive nitrogen flow a slurry of 5% Pt/C (1.13 g; 59.4% wet) in 3 mL THF is added via syringe (14-gauge needle) through the port. Additional THF (2 mL) is used to slurry remaining catalyst and added to the reaction. The port is closed and the autoclave pressurized to 75 psi with hydrogen and then slowly vented. This is repeated three times. The final hydrogen pressure is adjusted to 75 psi and the reaction mixture is hydrogenated overnight (12 hours) with the stirring maintained at 600 rpm. The vessel is then vented and subsequently pressurized with nitrogen (100 psi) and vented. The reactor is pressurized with nitrogen and vented three more times.

Under positive nitrogen flow 42 mL of ice-cold 12.4% hydrochloric acid (28 mL water+14 mL 37% HCl) is added slowly and the reaction mixture is stirred under nitrogen for 1 hour at 25° C. and 900 rpm and subsequently pressure transferred into a 250 mL Erlenmeyer flask. The hydrogenator is charged with toluene (50 mL) and 30 mL of 10% hydrochloric acid. The mixture is agitated for 30 minutes at 900 rpm and subsequently pressure transferred into an Erlenmeyer flask. The combined biphasic heterogeneous solution is filtered through a 1 cm Celite pad under vacuum to remove the Pt/C catalyst. The filter cake is further rinsed with aqueous 10% HCl (100 mL). The clear filtrate phase separates immediately and the organic layer is removed and discarded. Under stirring and cooling, 50 mL of toluene is added and the pH is adjusted to approximately 13 by slow addition of 50% NaOH (30 mL). The biphasic slurry is filtered through a 1 cm Celite pad to remove titanium salts. The filter cake is washed with toluene (2×50 mL), the layers are then separated and the toluene layer is concentrated at 80° C. until the volume of toluene is reduced to 20 mL. Then, 40 mL of n-heptane is added and the mixture is slowly cooled to 10° C. over 2–3 hours (0.5 g of seeds (~5%) is added at 55° C.). The precipitate is filtered, washed with 40 mL toluene/n-heptane 1/6 (v/v) and dried in vacuum at 40° C. The yield of colorless solids is 7.3 g, 61 % of theory.

What is claimed is:

1. A process for preparing (S,S)-cis-2-benzhydryl-3-benzylaminoquinuclidine comprising the steps of:

contacting a compound containing a mixture of R- and S-isomers and having the formula

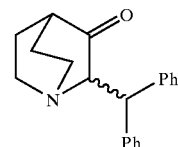

with an effective amount of a chiral organic acid in the presence of an organic solvent and an effective amount of an organic carboxylic acid for converting said R-isomer into an acid salt of said S isomer, said organic solvent being capable of solubilizing said compound containing said mixture of R- and S-isomers, while precipitating said acid salt and said organic carboxylic acid being different from said chiral organic acid;

neutralizing said acid salt with a base to provide an S-isomer of a chiral ketone of the formula

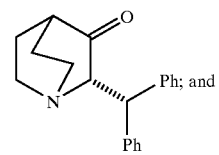

reacting said chiral ketone with an organic amine in the presence of a Lewis acid to provide the corresponding imine and reducing said imine.

2. The process of claim 1 wherein the compound is present as a racemic mixture.

3. The process of claim 1 wherein said acid salt is a tartrate salt of (2S)-benzhydryl-3-quinuclidinone.

4. The process of claim 1 wherein said chiral organic acid is L-tartaric acid.

5. The process of claim 1 wherein said effective amount of said chiral organic acid employed is at least one equilivant or more.

6. The process of claim 1 wherein said organic solvent is an alcohol.

7. The process of claim 5 wherein said alcohol is ethanol.

8. The process of claim 6 wherein said alcohol is a denatured alcohol.

9. The process of claim 1 wherein said organic carboxylic acid is acetic acid, propionic acid or butyric acid.

10. The process of claim 9 wherein said organic carboxylic acid is acetic acid.

11. The process of claim 1 wherein said effective amount of said organic carboxylic acid employed is at least one equivalent, relative to said compound.

12. The process of claim 1 wherein said base is sodium bicarbonate, potassium bicarbonate, sodium carbonate, potassium carbonate, sodium hydroxide or potassium hydroxide.

13. The process of claim 1 wherein said base is added with cooling to maintain a temperature below 25° C. until reaching a pH of about 9.

14. The process of claim 1 wherein said neutralizing is performed in the presence of a biphasic solvent mixture.

15. The process of claim 14 wherein said biphasic solvent mixture comprises a second organic solvent and water.

16. The process of claim 15 wherein said second organic solvent is toluene, ethyl acetate, or methyl t-butyl ether.

17. The process of claim 1 wherein said Lewis acid is an aluminum salt.

18. The process of claim 16 wherein said aluminum salt is aluminium triisopropoxide.

19. The process of claim 1 wherein said Lewis acid is a titanium salt.

20. The process of claim 19 wherein said titanium salt is titanium tetra-isopropoxide.

21. The process of claim 1 wherein at least one equivalent or more of said Lewis acid is employed relative to the S isomer of the chiral ketone.

22. The process of claim 1 wherein said imine is reduced by reacting the same with a reducing agent in the presence of a noble metal catalyst.

23. The process of claim 22 wherein said noble metal catalyst is a supported palladium or a supported platinum catalyst.

24. The process of claim 22 wherein said noble metal catalyst is platinum on carbon.

25. The process of claim 22 wherein said reducing agent is hydrogen.

26. The process of claim 1 wherein said organic amine is an arylalkylamine.

27. The process of claim 26 wherein said arylalkylamine is benzylamine.

28. The process of claim 1 wherein said acid salt is produced in a yield greater than 50%.

29. The process of claim 28 wherein said yield is from 85 to 90%.

30. The process of claim 1 wherein said imine is reduced immediately following formation of the same.

* * * * *